(12) United States Patent
Vilkomerson

(10) Patent No.: US 9,675,316 B2
(45) Date of Patent: Jun. 13, 2017

(54) FOCUSED ULTRASONIC DIFFRACTION-GRATING TRANSDUCER

(71) Applicant: DVX, LLC, Princeton, NJ (US)

(72) Inventor: David Vilkomerson, Princeton, NJ (US)

(73) Assignee: DVX, LLC, Princeton, NJ (US)

( * ) Notice: Subject to any disclaimer, the term of this patent is extended or adjusted under 35 U.S.C. 154(b) by 0 days.

(21) Appl. No.: 14/845,401

(22) Filed: Sep. 4, 2015

(65) Prior Publication Data

US 2016/0120498 A1    May 5, 2016

Related U.S. Application Data

(60) Provisional application No. 62/069,868, filed on Oct. 29, 2014.

(51) Int. Cl.
*A61B 8/00* (2006.01)
*A61B 8/06* (2006.01)
*A61B 8/08* (2006.01)

(52) U.S. Cl.
CPC .............. *A61B 8/06* (2013.01); *A61B 8/4494* (2013.01); *A61B 8/488* (2013.01); *A61B 8/0891* (2013.01)

(58) Field of Classification Search
CPC ....... A61B 8/06; A61B 8/0891; A61B 8/4455; A61B 8/4494; A61B 8/488; A61B 8/4483;

(Continued)

(56) References Cited

U.S. PATENT DOCUMENTS

| 5,540,230 A | 7/1996 | Vilkomerson |
| 5,797,845 A * | 8/1998 | Barabash ................ A61B 8/14 128/916 |

(Continued)

FOREIGN PATENT DOCUMENTS

WO    WO2012/148985 A1 *  11/2012

OTHER PUBLICATIONS

Chapter 12, Volumetric Blood Flow Measurement, in "Doppler Ultrasound" by Evans and McDicken, 2nd Ed, J. Wiley and Sons, New York 2000.

(Continued)

*Primary Examiner* — Amanda Lauritzen Moher
*Assistant Examiner* — Shahdeep Mohammed
(74) *Attorney, Agent, or Firm* — Fox Rothschild LLP

(57) ABSTRACT

Ultrasound diffraction-grating transducers produce beams at an angle to their face, which makes them useful for Doppler measurement of scattering fluids such as blood. The present invention discloses a diffraction-grating transducer, with the capability to focus transmitting or receiving beams to a desired point in space. This focusing capability leads to greater sensitivity when the diffraction-grating transducer is used as a receiver, and greater concentration of ultrasound energy when used as a transmitter. The focusing is achieved by using curved elements instead of the straight ones in conventional diffraction-grating transducers, and by using non-uniform spacing among these elements rather than the uniform spacing of conventional diffraction-grating transducers. Methods of computing the proper curvature of the elements and their spacing for a desired focal point in space are provided.

16 Claims, 4 Drawing Sheets

(58) Field of Classification Search
CPC . G01F 1/663; G01F 1/66; G01F 1/662; G01F 1/667; G01F 1/668; G01F 1/74; G01F 25/0007; G01N 29/024; G01N 29/036
See application file for complete search history.

(56) References Cited

U.S. PATENT DOCUMENTS

| | | | |
|---|---|---|---|
| 2012/0197129 A1* | 8/2012 | Vilkomerson | A61B 8/06 600/454 |
| 2013/0060140 A1* | 3/2013 | Sinelnikov | A61N 7/00 600/439 |

OTHER PUBLICATIONS

Chapter 6, Signal Detection and Processing: CW and PW Doppler, in "Doppler Ultrasound" by Evans and McDicken, 2nd Ed, J. Wiley and Sons, New York 2000.
D. Vilkomerson, S. Ricci, P. Tortoli, "Finding the Peak Velocity in a Flow from Its Doppler Spectrum", IEEE Transactions on Ultrasonics, Ferroelectrics, and Frequency Control, vol. 60, No. 10, Oct. 2013, p. 2079-2088.
Jonathan M. Cannata, PhD, Thomas Chilipka, Hao-Chung Yang, MS, Sukgu Han, MD, Sung W. Ham, MD,Vincent L. Rowe, MD, Fred A. Weaver, MD, K. Kirk Shung, PhD, David Vilkomerson, PhD, "Development of a Flexible Implantable Sensor for Postoperative Monitoring of Blood Flow," Journal of Ultrasound in Medicine 2012; vol. 31;1795-1802.
Robert T. Beyer, "From Sounds of Our Times: Two Hundred Years of Acoustics", Springer-Verlag New York, 1999, p. 88.

\* cited by examiner

FOCUSED ULTRASONIC DIFFRACTION-GRATING TRANSDUCER

CROSS-REFERENCE TO RELATED APPLICATIONS

This application claims the benefit of U.S. Provisional Application Ser. No. 62/069,868, filed on Oct. 29, 2014. The disclosure of the above application is incorporated herein by reference in its entirety for any purpose.

FIELD OF THE INVENTION

The present invention relates generally to an ultrasonic transducer, and particularly to a focused-diffraction-gate-transducer for the measurement of blood velocity and general imaging applications.

BACKGROUND OF THE INVENTION

An ultrasonic diffraction-grating transducer (DGT), which can be fabricated from piezoceramic, piezoplastic, or any piezoactive material, has the special capability of producing a beam at an angle to its face, as has been disclosed in U.S. Pat. No. 5,540,230 "Diffracting Doppler Transducer" ('230 patent, incorporated herein by reference) and has been used to measure blood velocity, e.g. Cannata J M et al, "Development of a Flexible Implantable Flow Sensor for Post-operative Monitoring of Blood Flow," Journal of Ultrasound in Medicine, 2012 vol 31, pp 1795-1802 (Cannata reference). The DGT's so described produce a uniform width beam of uniform angle, as shown in FIG. 1. Note beams maintain constant width.

The DGT structure has been useful, particularly for Doppler applications, where its special angled-beam characteristic allows it to be placed on the wall of a vessel and its beam to have a component in the direction of flow in that vessel, allowing Doppler measurements. However, its broad uniform-width beam limits its applications. For example, its broad beam structure, when used as a transmitter, cannot produce a high-resolution image because its "spot size" is large. When used as a receiver, it can only detect energy arriving in the narrow range of angles corresponding to its beam angle—so it is not very sensitive to ultrasound scattered from a point scatterer, e.g. a red blood cell, that spreads the energy it scatters in waves propagating over a wide range of angles.

A focusing device offers the advantage of greater sensitivity as a receiver (because a lens system gathers energy over range of angles) and greater intensity creation as a transmitter because of its focusing action. The importance of focusing ultrasound has led to the development of phased-array ultrasound systems that are the most often used clinical ultrasound imaging systems. These systems use individually connected small ultrasound transducers elements: by firing the elements at carefully chosen different times they can form a focused transmit beam, and by adding individually calculated phase shifts to the signal from each transducer form a focused receive beam. Such systems, requiring separate send and receive channels and cables for each element in the array, which can number in the hundreds or thousands, require expensive transducers, cables to the transducers, and complex circuitry.

DGT's were developed to be transducers that could produce angled beams with a single cable and channel connection. The present invention discloses a DGT that retains the capability of producing an angled beam from a single cable and signal channel, but of increased capability because of its focused transmitting and receiving capability. It is therefore an object of the present invention to improve DGT's so that they have the capability of focusing like conventional phased-array transducers while retaining the capability of producing an angled beam from a single cable and signal channel. It is another object of the present invention to use the focused-DGT for measuring velocity of blood flow in a vessel and imaging applications.

SUMMARY OF INVENTION

We disclose here a new DGT structure that makes it possible to form a focused beam from a DGT. We teach how to shape and space the array elements that form the DGT, so that a DGT can produce a focused ultrasound beam. Used as a receiver, the new DGT structure receives ultrasound over a much larger range of angles, achieving much greater sensitivity to ultrasound scattered by a point, e.g. a red blood cell in blood flowing through a lumen. Used as a transmitter, it can produce a tightly focused spot. The DGT with focusing capability is called an F-DGT, for Focused Diffraction-Grating-Transducer.

DETAILED DESCRIPTION OF THE PREFERRED EMBODIMENTS

Figure 1:
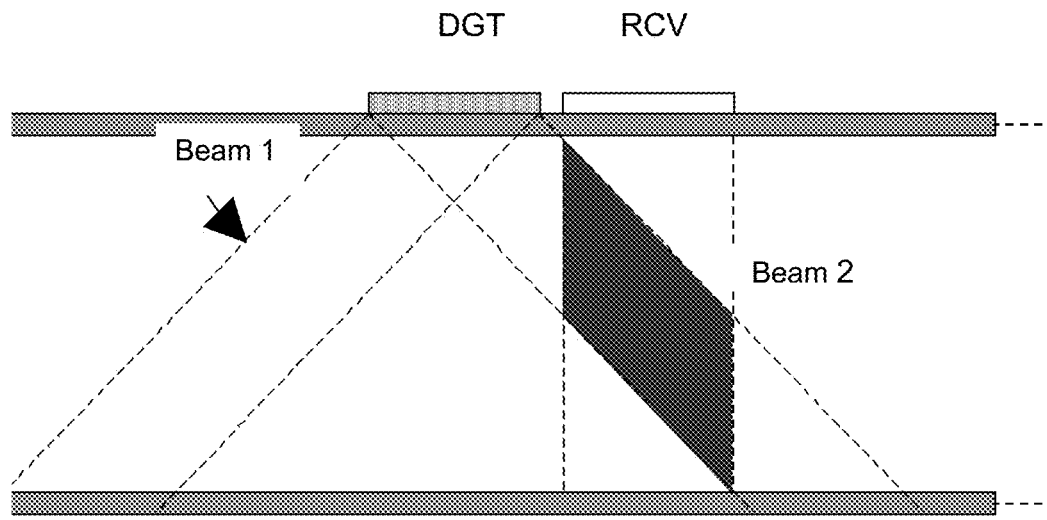
FIG. 1 shows Doppler velocity measurement using the conventional DGT (from Cannata reference).
Figure 2:
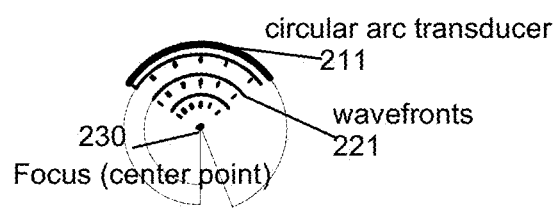
FIG. 2 shows a circular arc transducer according to one aspect of the present invention.

Focusing a wavefront means concentrating all the energy in a wavefront to a single location, known as the focal point. (For example, when a lens concentrates the energy of sunlight onto a single, much brighter point that can start a fire.) This concentration is achieved by adjusting the phase of each part of the wavefront (as is performed by the lens in the example above) so that the wavefront is curved so that it converges at the focal point. For example, as shown in FIG. 2, a transducer, 211 is made of a portion of a circle and produces wavefronts 221 that converge at the center of the circle segment 230, i.e. as a circle is defined as the locus of points of equal distance from a central point, waves launched at the same time from the circumference of a circle propagating at the same velocity are in the same phase when they reach the central point of the circle; all the waves launched from the circle being in phase add in amplitude at one point—i.e. are focused.

Figure 3:
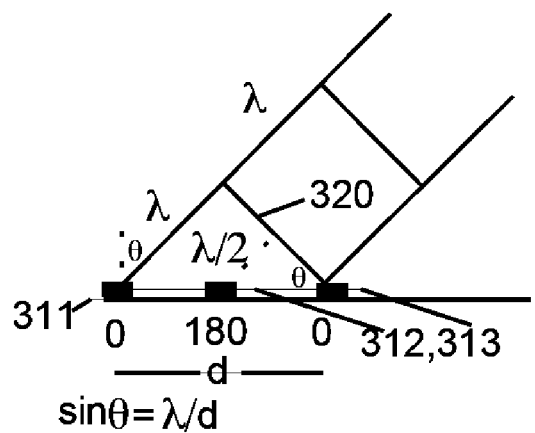
FIG. 3 shows generating the beam in a conventional DGT.

The principle of constructive interference, i.e. when waves arising from a series of point source (known as Huygen's wavelets) are in phase, is how conventional DGT's form their beam. U.S. Pat. No. 5,540,230, Diffracting Doppler Transducer describes in detail how a conventional DGT forms its beam. With reference to FIG. 3, the active elements 311, 312 and 313, with the spatial period d, produce a beam at angle θ. These elements, in said "properly spaced" linear array, are driven in alternating phase, i.e. at 0° and 180°; along the line 320 the wave from element 311 has traveled one λ, and is the same phase as from element 313; waves from the element 312 halfway between has traveled only λ/2, but because it was launched 180° behind the waves from 311 and 313, it is of the same phase. The wavefront 320 is at the angle θ, where, as can be seen from the triangle of side d and λ, sin θ=λ/d. The linear elements in a conventional DGT, as described in '230, are uniformly spaced, so all the wavefronts launched are uniform across the DGT and these wavefronts, being parallel, propagate as a uniform beam, neither expanding nor contracting. When double beam is used, the element spacing, d, for double-beam DGT will double the spacing for single-beam DGT as explained in detail in '230.

Figure 4:
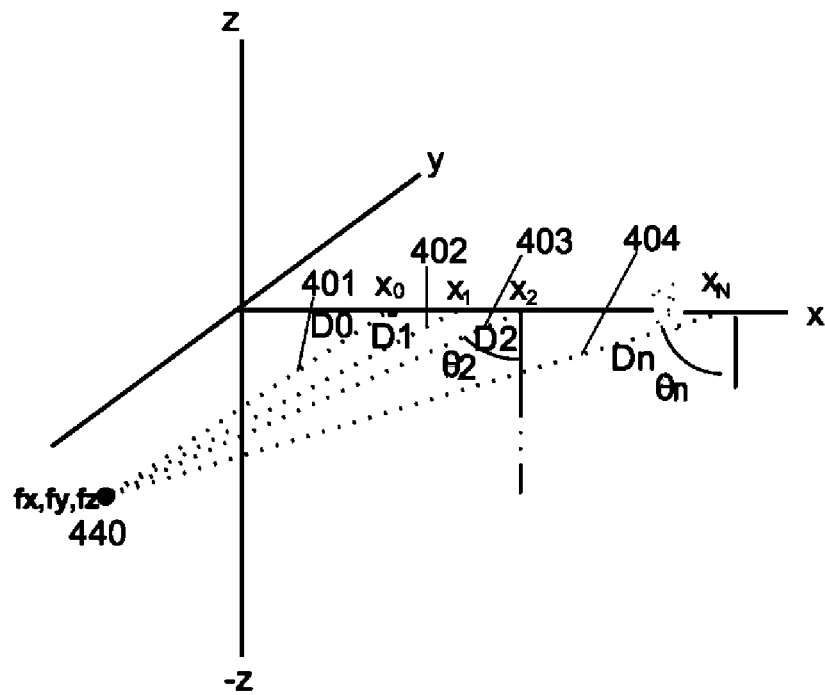
FIG. 4 shows the center points of the elements for an F-DGT array according to one aspect of the present invention.

In order to form a focused, i.e. converging, beam, bringing the energy from all the elements of the array to the focal point, we must change the spatial period d of the elements so that, rather than being equally spaced at d=λ/sin θ, they are spaced so that, as shown in FIG. 4, the Huygen's wavelets from each element driven with alternating phase arrives at the focal point, 440, in phase (This is like the Huygen's wavelets arriving in phase along the wavefront 320 in FIG. 3). Therefore, successive midpoint of the circular elements, i.e. x0, x1, etc, which result in distances 401, 402, etc, must be spaced in such a way that each distance be λ/2 (so that the 180° phase drive is compensated) more than that of the previous element, i.e. D1, 402, is λ/2 longer than 401 D0, and D2, 403, is λ/2 longer than D1, etc until the final midpoint of element xn, for which its distance Dn, 404, is λ/2 is more than the previous distance. Therefore, we can calculate the positions of the middle points of circular elements by satisfying this condition.

With reference to FIG. 4, in the x-z plane in the space shown, assume the desired focal point is at −fz, −fx, as shown, and the first element on the x-axis, chosen to be adjacent to the region where the focal point is to be placed, but where the element will not obstruct the insonifying beam, we will call $x_0$. We can compute the distance of this central point of the element from the focal point by using the Pythagorean theorem: i.e. $((x_{0+fx})^2+fz^2)^{1/2}$. The next element, at $x_1$, should be placed so its distance to the focal point is greater by λ/2; therefore we can find the position for $x_1$ by solving $[(x_1+fx)^2+fz^2]^{1/2}=[(x_0+fx)^2+fz^2]^{1/2}+\lambda/2$ (Eq. 1) for $x_1$. The next element $x_2$ is found from the position of $x_1$ by substituting $x_2$ in place of $x_1$ and $x_1$ in place of $x_0$. In this way the position of all the elements in the desired size array can be iteratively calculated, that is each position calculated from the previous one so that each element's distance to the focal point is λ/2 greater than the previous element's distance.

This calculation establishes where the elements are on the x-axis. To make the elements focus at that focal point, all the parts of array elements, not just their center points on the x-axis, must be at the same distance to the desired focal point as the center point.

As shown in FIG. 2, all points on an arc-segment of a circle of a particular radius are at the same distance, i.e. the radius of curvature, from its center. Therefore, to focus at the desired focal point, which is on the x-z plane at a fixed distance from z-axis, the elements are formed to be arcs of a circle whose radius is equal to the distance from the z-axis, i.e. the computed $x_0$'s; therefore, the entire arc-segment element must be at the same distance to the focal point. As shown in Eq. 1, as the next array element is placed further away from the z-axis, i.e. centered at $x_1$, its distance to the focal point increments by λ/2, so on and so forth.

Figure 5:
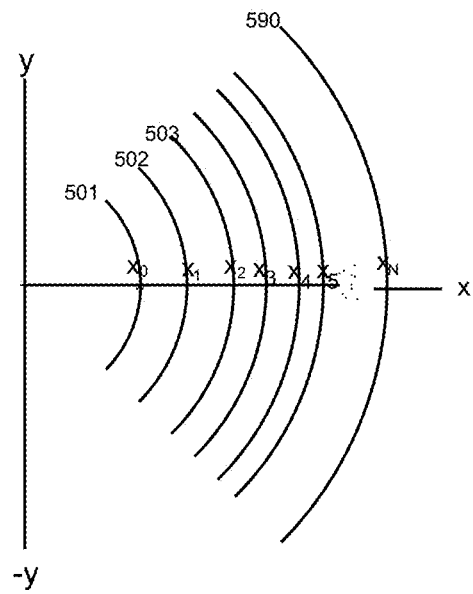
FIG. 5 shows the top view of a F-DGT according to one aspect of the present invention.

With reference to FIG. 5, the top view of a F-DGT is shown. The structure of the F-DGT comprises an array of a series of parallel circular sections, e.g. 501, 502, . . . to 590 etc, with a common center of curvature and spaced at the $x_n$ intervals (center points shown in FIG. 4). As the angle of the "ray" (using the term ray as it is used in optics to show the perpendicular to the wavefront, as in "ray tracing") gets larger, as seen in FIG. 4, θn>θ2, then sin θ increases. Therefore, according to d=λ/sin θ, d decreases.

The F-DGT described here assumes a flat plane. However, the very same principle, i.e. determining the position of the array elements and their shape by making the distance from each point on the element to the focal point the same, and ultrasound from each element in the array arrive λ/2 later than from the previous closer element, can be applied to a non-flat surface. In this case, the distance to the focal point is calculated from the element position and shape and the x, y, z coordinates of the non-flat plane on which the element is placed. While the calculation is more complicated, the principle of design is the same as disclosed above.

An Exemplary Embodiment

Figure 6:
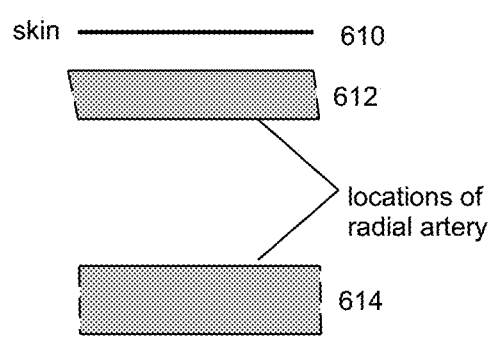
FIG. 6 shows the use of F-DGT for Doppler velocity measurement of blood flowing through a lumen in the radial artery that may be shallow or deep beneath the skin, according to one exemplary embodiment of the present invention.

With reference to FIG. 6, an example is shown as to why the increased sensitivity of a F-DGT may be needed in order to monitor the velocity of blood flowing through a lumen in a radial artery. As shown, the blood vessel, a few mm in diameter, may be from 1 to 7 mm below the skin surface 610; the vessel can be shallow at 612, or deep, at 614. To meet this end, as shown in FIG. 7, one F-DGT (elements 741 to 749), focuses to point 740 to cover the possible deep arterial positions, whereas the other F-DGT (elements 751 to 759), is focused more shallowly at 750 to cover more shallow arterial positions.

Figure 7:
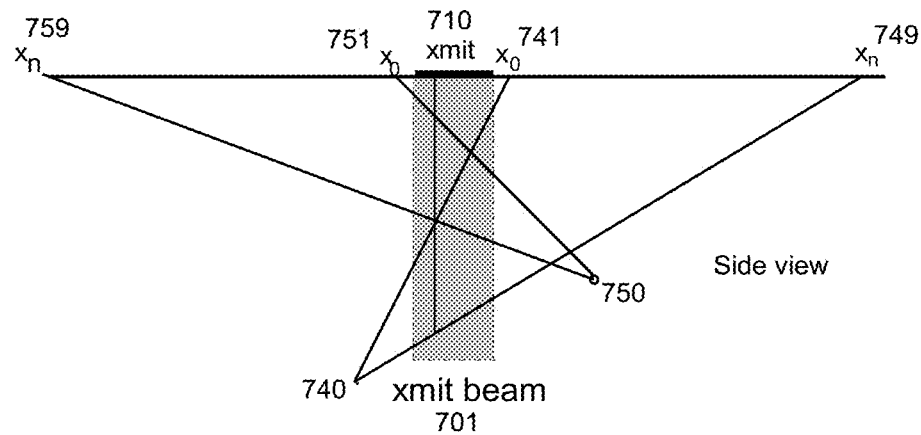
FIG. 7 shows a schematic representation of the exemplary embodiment F-DGT for clinical requirement of FIG. 6.

According to one aspect of the present invention, with reference to FIG. 7, the transducer comprises a simple slab ceramic transducer (as transmitter, i.e. Xmit), 710, placed where a pulse is felt, and produces a narrow beam going straight down. Disposed on one side of the transmitter is a F-DGT, shown to the right of the transmitter and designed to focus at point 740, that receives scattered ultrasound from the deep region of the volume to be covered. On the opposite of the transmitter is the F-DGT configured to focus at point 750, which receives scattered ultrasound from the more shallow part of the region of interest. The F-DGT's are designed by the procedure described by Eq. 1 above. In this example, the shallow focal point 750 is at fz=−5, fx=−4.2; for the deep-receiving region, fz=−8, fx=−1.5. These focal points have been chosen so that the beams from the first and last elements (determined by the desired size of the array per application) converge at the chosen focal points and cover the region where the radial artery is found, with some overlap.

Using both areas of insonation, signals arising from the entire region where the radial artery can be found, between 1 and 7 mm below the skin, will be detected by the F-DGT's. According to another aspect of the present invention, the two F-DGT's can also be placed on the same side of the transducer, but as one F-DGT would therefore be further from the transmitter the signals it would receive would be attenuated by the longer path length.

According to one aspect of the present invention, twenty MHz is used for the ultrasound frequency as it enables good signal levels—blood scatters ultrasound at the $4^{th}$ power of the frequency—without too much attenuation (attenuation in dB/cm increases linearly with frequency). As understood by a person having ordinary skill in the art, different frequencies would best suit different situations.

Figure 8:
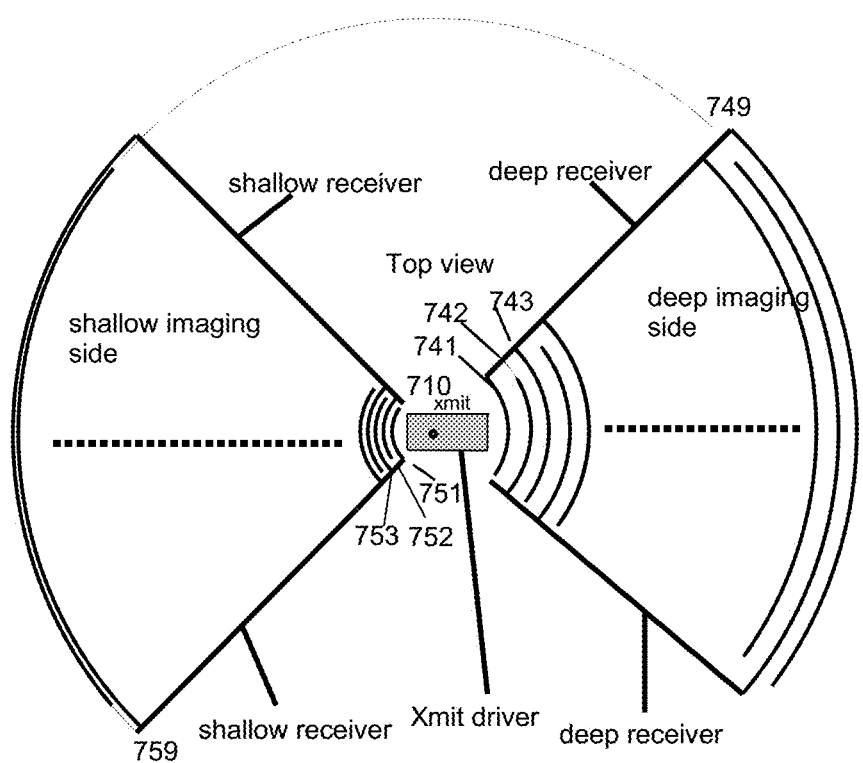
FIG. 8 shows the position of the center points of the arc-segments of exemplary embodiment of FIG. 7 according to one aspect of the present invention.

In one exemplary embodiment of the present invention, with reference to FIG. 8, on the shallow side, element 751 corresponds to x0, element 752 to x1 and so on, until element 759 corresponds to x243 at 11.027 mm from the center. Similarly, on the deep side, element 741 corresponds to x0, element 749 to x164, 11.005 mm. The radius of curvature of each element corresponds to its position. Taking an example of $\lambda=0.075$ mm, corresponding to 20 MHz in tissue, with reference to FIGS. 7 & 8, the midpoints on the x-axis, which correspond to the radius of curvature of the elements, are shown in the table below for the first 15 positions and the last position on each side. The spacing between the elements is quite different as the wavefronts from the right side, focusing deeply, are at a smaller angle θ to the transducer face than those from the left (imaging the shallow region) as is visible in FIG. 4.

| Shallow-focusing Element Position (mm) | | Deep-focusing Element Position (mm) | |
|---|---|---|---|
| X0 | 1.000 | X0 | 2.000 |
| X1 | 1.053 | X1 | 2.096 |
| X2 | 1.106 | X2 | 2.188 |
| X3 | 1.158 | x3 | 2.278 |
| X4 | 1.210 | x4 | 2.367 |
| X5 | 1.262 | x5 | 2.454 |
| X6 | 1.314 | x6 | 2.540 |
| X7 | 1.365 | x7 | 2.624 |
| X8 | 1.416 | x8 | 2.707 |
| X9 | 1.467 | x9 | 2.788 |
| X10 | 1.518 | x10 | 2.869 |
| X11 | 1.569 | x11 | 2.948 |
| X12 | 1.619 | x12 | 3.026 |
| X13 | 1.669 | x13 | 3.103 |
| X14 | 1.719 | x14 | 3.179 |
| X15 | 1.769 | x15 | 3.254 |
| X242 | 10.989 | X163 | 10.960 |
| X243 | 11.028 | X164 | 11.005 |

As shown in FIG. 8, the alternating phase elements, e.g. 741 and 742, are connected to separate bus bars that connect similar-phase elements together on each side of the fan shape circular array. As previously taught in '230 and as described in the Cannata reference, by polarizing the piezoactive material in opposite directions, the two phases can be interconnected.

These array elements are shown as "lines" in the FIGS. 5 and 8—in actual arrays, the electrodes have finite width. Wider elements intercept more scattered energy, but, as is well known in the transducer art, have a narrower range of angular acceptance; therefore, a usual compromise is to make the width of the electrodes roughly half the spacing (See Cannata reference). For example, if the spacing is 100 microns, the electrodes are ~50 microns wide. This leads to equal-width electrodes and spaces between the electrodes, which is easy to fabricate and analyze. However, variation from this half-spacing, for example, to tune the electrical capacitance of the array or in fabrication, will not have a major effect on the operation of the F-DGT.

The arcs of the F-DGT array elements in the exemplary embodiment of FIG. 7 cover ±45°; smaller arcs could be used, but as they would cover less area, the sensitivity would be less, though easier to make.

Greater than ±45°, up to ±90° are also possible. However, as the Doppler shift frequency is proportional to the cosine of the angle between the flow and the detecting angle, at high angles all the velocities in the flow would be compressed to low frequencies (zero at 90°!). As is well-known in the Doppler field, low frequencies are not useful because motion artifacts, 60 Hz and its harmonics interfere at those frequencies, so high arc angles, besides increasing the size and fabrication complexity, would often not contribute to the desired signal.

The discussion and the exemplary embodiment assume a double-beam DGT's (as described in the '230 patent). Double beam DGT's, which produce two beams at equal angles, are more easily made and driven, as explained in '230. However, single-beam DGT's, which require 4 elements per periodicity d rather than the two elements of the double beam DGT and therefore harder to fabricate, can also be used with an increase in sensitivity. The design for the single beam F-DGT is similar to the double beam, except, as the phase change per element is $\lambda/4$ for the single beam rather than $\lambda/2$ for the double beam, Eq. 1 would be modified to replace the term $\lambda/2$ by $\lambda/4$.

For either double-beam or single beam method, the received ultrasound signal is received by the F-DGT(s), with the total received power proportional to the area of the electrodes shown in FIG. 7. The received signal is also proportional to the power transmitted that strikes the scatterers (for blood, the red blood cells). The shift in frequency from the transmitted ultrasound frequency is proportional to how many scatterers are moving at a particular velocity, so when the signal is amplified, heterodyne-detected with transmitted frequency, and the resulting Doppler signal is processed by an FFT, the resulting power spectrum contains the information needed to determine velocity and flow. Typical circuits to perform these processes are described in detail in Chapter 6, "Signal Detection and Processing: CW and PW Doppler", and systems to determine blood volume flow from Doppler in Chapter 12, "Volumetric Blood Flow Measurement", Evans and McDicken, Doppler Ultrasound, $2^{nd}$ Edition, John Wiley & Sons, Chichester, 2000. The Doppler power spectrum can be analyzed to determine the peak velocity present in the flow, for example, by the methods described in "Finding the Peak Velocity in a Flow from Its Doppler Spectrum", IEEE Transactions on Ultrasonics, Ferroelectrics, and Frequency Control, vol. 60, no. 10, October 2013, 2079, by Vilkomerson, et al.

Although continuously changing array-element spacing is disclosed, it is recognized that using a sequence of short sequences of uniformly-spaced array elements can approximate the focusing desired, i.e. as a series of uniform beams at increasing angles crossing in the region of interest. Such a configuration, however, is less of optimal sensitivity or focusing capability.

Alternative Embodiments

The present invention could be designed for other depths and other focal arrangements using the general design principles disclosed above. For example, with reference to FIG. 7, only one F-DGT is needed if only a narrow range of depth is desired. Similarly, if greater range of depth or more focal areas desired, multiple F-DGT's can be used on both sides (or one side, depending on the measurement situation)

of the transmitter. As these F-DGT's would be further away from the transmit beam, the signals they would receive would be weaker. If single-beam F-DGT's were used, they would receive from only from one direction, so multiple pairs of single-beam DGT's and transmit beams could be used to cover greater volume.

In another embodiment of the present invention, the F-DGT can be used as an imaging system rather than only for Doppler uses. The F-DGT acts as a focused insonating source as well as a focused receiver, with a piezoceramic or piezoplastic, or other piezoactive material used for a transducer for either receiving the signal or producing the insonation, similarly to the way a lens can be used for both focused illumination or forming an image. The electrode structure shown in FIG. 7 both detects and insonates. Thus, an F-DGT following the design rules as discussed with regard to FIG. 4, and if pulsed or continuously excited, would produce a spot of ultrasound energy at the focal point 440 in FIG. 4. As the backscattered signal from that point would be received by the same F-DGT, the signal strength would indicate the reflectivity of the material at that focal point. If the F-DGT were translated slightly (or the imaging subject translated slightly) and the process repeated, the ultrasonic reflectivity of the point next to 440 would be determined, and by scanning the F-DGT over an area (or scanning the object whose acoustic reflectivity is to be mapped under the F-DGT), a reflectivity map, an image, would be obtained. This is similar to the way acoustic microscopes operate, but with an F-DGT rather than the conventional focused ultrasound transducer.

An F-DGT can be used as described for imaging by pulse-echo, or by transmission imaging, where separate F-DGT's would be used, in the same way conventional focused ultrasound transducers are, with one F-DGT acting as a transmitter and one as a receiver.

The transmitter and receiver can be interchanged under the well-known general theory for wave propagation called reciprocity theorem, under which " . . . vibration by a simple source of sound of given period and intensity, the variation of pressure is the same at any point B when the source of sound is at A as it would have been at A had the source of sound been situated at B." R. T. Beyer, "Sounds of Our Times: Two Hundred Years of Acoustics," Springer-Verlag, New York 1999, page 88 (quoting Lord Rayleigh, Proc. Royal Society (London) 25, 118-122 (1876)). Also see Wikipedia http://en.wikipedia.org/wiki/Reciprocity_(electromagnetism). A well-known example of that theory is that the transmitting and receiving patterns of an antenna are the same. As can be enabled under the reciprocity theorem, without changing aforementioned structure of the transducer, the F-DGT transducer can be used to transmit ultrasound, rather than receiving it, and the Xmit circuit can be used to receive ultrasound.

There are many other variations obvious to one skilled-in-the-art not described herein for use of the F-DGT apparatus and method disclosed here. The examples and disclosures herein are not meant to be exhaustive but rather to indicate the different ways those skilled in the art will be able to utilize the present invention to make accurate measurement of blood or as an imaging application. For example, the transmitting beam or receiving beam from the slab transducer does not have to be exactly perpendicular to the lumen, but rather, being essentially perpendicular suffices as long as the basic and novel characteristics of the focused-DGT is not affected.

Further variations, including combinations and/or alternative implementations, of the embodiments described herein can be readily obtained by one skilled in the art without burdensome and/or undue experimentation. Such variations are not to be regarded as a departure from the spirit and scope of the invention.

What is claimed is:

1. An ultrasound transducer for measuring a velocity of flow in a lumen having an axis, comprising:
   a transmitter configured to excite an ultrasound beam perpendicular to the axis of the lumen; and
   a diffraction-grating transducer (DGT) disposed adjacent to the transmitter, said DGT comprising a fan shape receiver, said receiver comprising an array of circular segment elements that form a receiving beam, each circular segment element being disposed around a common center point and at a radius from said common center point, wherein any two neighboring circular segment elements in said array are spaced at a non-uniform spacing, wherein a difference in distances from a desired focal point inside the lumen to each of the neighboring circular segment elements is $\lambda/2$, wherein $\lambda$ is the wavelength of the ultrasound beam, and wherein wavefronts of said receiving beam converge to the desired focal point.

2. The ultrasound transducer of claim 1, wherein the ultrasound beam forms a transmitting beam region and the desired focal point is outside the transmitting beam region.

3. The ultrasound transducer of claim 1 further comprises two bus bars disposed on each side of the fan shape receiver, each said bar connecting to alternating circular segment elements of said array of circular segment elements.

4. The ultrasound transducer of claim 1, wherein the transmitter is a slab transducer.

5. A method of measuring velocity of blood containing ultrasound scatterers flowing through a lumen having an axis, using an ultrasound transducer comprising: a transmitter; a diffraction-grating transducer (DGT) disposed adjacent to the transmitter, said DGT comprising a fan shape receiver that includes an array of circular segment elements, each circular segment element being disposed around a common center point and at a radius from said common center point, wherein any two neighboring circular segment elements in said array are spaced at a non-uniform spacing, wherein a difference in distances from a desired focal point in the lumen to each of the neighboring circular segment elements is $\lambda/2$, wherein $\lambda$ is a wavelength, said method comprising the steps of:
   exciting from the transmitter an ultrasound beam with the wavelength of $\lambda$, the ultrasound beam being perpendicular to the axis of the lumen;
   receiving from the DGT signals from the ultrasound beam excited from the transmitter; and
   determining the velocity of blood based on shifted frequency in said received signals, wherein said shifted frequency is caused by the scatterers flowing through the lumen.

6. The method of claim 5, wherein the ultrasound beam forms a transmitting beam region and the desired focal point is outside the transmitting beam region.

7. The method of claim 5, wherein the DGT further comprises two bus bars disposed on each side of the fan shape receiver, each said bar connecting to alternating circular segment elements of said array of circular segment elements.

8. The method of claim 5, wherein the transmitter is a slab transducer.

9. An ultrasound transducer for measuring a velocity of flow in a lumen having an axis, comprising:

a diffraction-grating transducer (DGT), said DGT comprising a fan shape transmitter, said transmitter comprising an array of circular segment elements configured to excite an ultrasound beam, each circular segment element being disposed around a common center point and at a radius from said common center point, wherein any two neighboring circular segment elements in said array of circular segment elements are spaced at a non-uniform spacing, wherein a difference in distances from a desired focal point inside the lumen to each of the neighboring circular segment elements is $\lambda/2$, wherein $\lambda$ is the wavelength of the ultrasound beam, and wherein wavefronts of said ultrasound beam converge to the desired focal point inside the lumen; and a receiver disposed adjacent to the DGT that form receiving beam perpendicular to the axis of the lumen.

10. The ultrasound transducer of claim 9, wherein the receiving beam forms a receiving beam region and the desired focal point is outside the receiving beam region.

11. The ultrasound transducer of claim 9 further comprising two bus bars disposed on each side of the fan shape transmitter, each said bar connecting to alternating circular segment elements of said array of circular segment elements.

12. The ultrasound transducer of claim 9, wherein the receiver is a slab transducer.

13. An ultrasound transducer for measuring a velocity of flow in a lumen of a radial artery beneath a skin surface, said lumen having an axis, comprising:

a transmitter configured to excite an ultrasound beam perpendicular to the axis of the lumen;

a first diffraction-grating transducer (DGT) disposed adjacent to one side of the transmitter, said first DGT comprising a first fan shape receiver, said first fan shape receiver comprising a first array of circular segment elements that form a first receiving beam, each circular segment element in the first array being disposed around a common center point and at a radius from said common center point, wherein any two neighboring circular segment elements in said first array of circular segment elements are spaced at a non-uniform spacing, wherein a difference in distances from a first desired focal point inside the lumen to each of the neighboring circular segment elements is $\lambda/2$, wherein $\lambda$ is the wavelength of the ultrasound beam, and wherein wavefronts of said first receiving beam converge to the first desired focal point; and a second diffraction-grating transducer (DGT) disposed adjacent to the opposite side of the transmitter from the first DGT, said second DGT comprising a second fan shape receiver, said second fan shape receiver comprising a second array of circular segment elements that form a second receiving beam, each circular segment element in the second array being disposed around the common center point and at a radius from said common center point, wherein any two neighboring circular segment elements in said second array of circular segment elements are spaced at a non-uniform spacing, wherein a difference in distances from the second desired focal point inside the lumen to each of the neighboring circular segment elements is $\lambda/2$, and wherein wavefronts of said second receiving beam converge to the second desired focal point;

wherein the first and second desired focal points are of different distances below the skin surface.

14. The ultrasound transducer of claim 13, wherein the ultrasound beam forms a transmitting beam region and the first and second desired focal points are outside the transmitting beam region.

15. The ultrasound transducer of claim 13, wherein each of the first and second DGT's further comprises two bus bars disposed on each side of the respective first or second fan shape receiver, each said bar connecting to alternating circular segment elements of said respective first or second array of circular segment elements.

16. The ultrasound transducer of claim 13, wherein the transmitter is a slab transducer.

* * * * *